United States Patent [19]
Johns et al.

[11] Patent Number: 5,658,268
[45] Date of Patent: Aug. 19, 1997

[54] ENHANCED WET SIGNAL RESPONSE IN ABSORBENT ARTICLES

[75] Inventors: Eric Mitchell Johns, Roswell; Clifford Jackson Ellis, Woodstock; Susan Carol Paul, Alpharetta, all of Ga.

[73] Assignee: Kimberly-Clark Worldwide, Inc., Irving, Tex.

[21] Appl. No.: 558,570

[22] Filed: Oct. 31, 1995

[51] Int. Cl.$^6$ .............................. A61F 13/15; A61F 13/20
[52] U.S. Cl. ..................... 604/361; 604/358; 604/378; 604/385.1
[58] Field of Search ................................. 604/358, 361, 604/378–381, 384, 385.1

[56] References Cited

U.S. PATENT DOCUMENTS

| | | |
|---|---|---|
| Re. 32,026 | 11/1985 | Yamashita et al. |
| 1,481,208 | 1/1924 | Johnson. |
| 2,261,473 | 11/1941 | Jennings. |

(List continued on next page.)

FOREIGN PATENT DOCUMENTS

| | | |
|---|---|---|
| 803714 | 1/1969 | Canada. |
| 2040602 | 10/1991 | Canada. |
| 1322940 | 10/1993 | Canada. |
| 0320991A2 | 6/1989 | European Pat. Off.. |
| 1192871 | 8/1989 | Japan. |
| 2244201 | 11/1991 | United Kingdom. |
| 2259018 | 3/1993 | United Kingdom. |
| 86/04219 | 7/1986 | WIPO. |
| 92/03113 | 3/1992 | WIPO. |
| 93/09742 | 5/1993 | WIPO. |
| 93/09746 | 5/1993 | WIPO. |
| 93/17648 | 9/1993 | WIPO. |
| 93/19716 | 10/1993 | WIPO. |
| 93/24085 | 12/1993 | WIPO. |
| 94/10958 | 5/1994 | WIPO. |

OTHER PUBLICATIONS

ASTM D 1238–90b—Standard Test Method for Flow Rates of Thermoplastics by Extrusion Plastomer–pp. 272–275 Sep. 1994.
ASTM E 794–85 (Reapproved 1989)—Standard Test Method for Melting and Crystalization Temperatures by Thermal Analysis–pp. 584–586 Sep. 1994.
Dow Corning "Silicone Wetting Agents for Textile Applications" Fact Sheet, 1992 Dow Corning Corporation.
ICI Americas Inc. "Technical Bulletin for Ahcovel® Base N–62 Liquid Nonionic Textile Softener", Copyright 1978 ICI Americas, Inc.
ICI RAYCA Technical Bulletin for MILEASE HPA, CA 706, Sep. 1990, ICI Americas Inc., Mt. Holly, N.C.
ICI RAYCA Technical Bulletin for MILEASE T, CA 701, Sep. 1990 ICI Americas Inc., Mt. Holly, N.C.
ICI RAYCA MILEASE® T. Finishing Agent Technical Sheet, Sep. 1989, ICI Specialty Chemicals, Wilmington, Delaware.
ICI RAYCA "Quality Auxiliaries for the Textile Industry, A Guide to Selection", Sep. 1991, ICI Surfactants, Mt. Holly, N.C.
ICI RAYCA "Textile Solutions . . . Fiber to Fabric", Oct. 1991, ICI Surfactants, Mt. Holly, N.C.
ICI Surfactants—Catalogue of Surfactants and Derivatives, Ref. No. 50–3E/8167–191, Jun. 1993, published by ICI Europe Limited, Everslaan 45, B–3078, Everberg, Belgium.
Material Safety Data Sheet for Developmental Products, ICI Americas Inc., 1991.

(List continued on next page.)

Primary Examiner—P. Zuttarelli
Attorney, Agent, or Firm—Patrick C. Wilson; Nicholas N. Leach; James B. Robinson

[57] ABSTRACT

Disclosed herein a personal care absorbent article which when first insulted, has a high initial surface moisture value which is maintained for several minutes but then, after a short period of time, drops to a lower value. As a result, the product has an initial "wet" feel but quickly changes to a "drier" feel so as to provide more comfort long term to the wearer.

19 Claims, 2 Drawing Sheets

U.S. PATENT DOCUMENTS

| | | |
|---|---|---|
| 2,907,173 | 10/1959 | Robbins . |
| 3,175,558 | 3/1965 | Caillouette et al. . |
| 3,276,944 | 10/1966 | Levy . |
| 3,338,992 | 8/1967 | Kinney . |
| 3,341,394 | 9/1967 | Kinney . |
| 3,423,266 | 1/1969 | Davies et al. . |
| 3,502,538 | 3/1970 | Petersen . |
| 3,502,763 | 3/1970 | Hartmann . |
| 3,542,615 | 11/1970 | Dobo et al. . |
| 3,561,447 | 2/1971 | Alexander . |
| 3,613,687 | 10/1971 | Kennedy . |
| 3,661,142 | 5/1972 | Flam . |
| 3,675,654 | 7/1972 | Baker et al. . |
| 3,692,618 | 9/1972 | Droschner et al. . |
| 3,791,849 | 2/1974 | Hammer et al. . |
| 3,802,817 | 4/1974 | Matsuki et al. . |
| 3,809,096 | 5/1974 | York . |
| 3,838,692 | 10/1974 | Levesque . |
| 3,860,003 | 1/1975 | Buell . |
| 3,973,068 | 8/1976 | Weber . |
| 3,976,049 | 8/1976 | Yamashita et al. . |
| 3,977,202 | 8/1976 | Forusz et al. . |
| 3,980,070 | 9/1976 | Krupa . |
| 4,022,211 | 5/1977 | Timmons et al. . |
| 4,073,852 | 2/1978 | Mesek . |
| 4,081,256 | 3/1978 | Donnelly . |
| 4,092,454 | 5/1978 | Domoto et al. . |
| 4,106,001 | 8/1978 | Mahoney . |
| 4,240,416 | 12/1980 | Boich . |
| 4,295,517 | 10/1981 | Guex et al. . |
| 4,302,853 | 12/1981 | Mesek . |
| 4,340,563 | 7/1982 | Appel et al. . |
| 4,419,403 | 12/1983 | Varona . |
| 4,573,447 | 3/1986 | Thrash et al. . |
| 4,615,695 | 10/1986 | Cooper . |
| 4,639,390 | 1/1987 | Shoji . |
| 4,639,949 | 2/1987 | Ales et al. . |
| 4,640,284 | 2/1987 | Ruderian . |
| 4,641,381 | 2/1987 | Heran et al. . |
| 4,642,819 | 2/1987 | Ales et al. . |
| 4,646,362 | 3/1987 | Heran et al. . |
| 4,655,877 | 4/1987 | Horimoto et al. . |
| 4,773,863 | 9/1988 | Douglas, III . |
| 4,773,903 | 9/1988 | Weisman et al. . |
| 4,786,530 | 11/1988 | Fox . |
| 4,789,588 | 12/1988 | Suzuki et al. . |
| 4,789,592 | 12/1988 | Taniguchi et al. . |
| 4,794,002 | 12/1988 | Henis et al. . |
| 4,854,332 | 8/1989 | Hanakura . |
| 4,865,596 | 9/1989 | Weisman et al. . |
| 4,885,204 | 12/1989 | Bither et al. . |
| 4,888,238 | 12/1989 | Katz et al. . |
| 4,923,454 | 5/1990 | Seymour et al. . |
| 4,924,084 | 5/1990 | Lask et al. . |
| 4,940,464 | 7/1990 | Van Gompel et al. . |
| 4,960,414 | 10/1990 | Meyer . |
| 4,987,908 | 1/1991 | Sprinkel et al. . |
| 5,019,066 | 5/1991 | Freeland et al. . |
| 5,026,364 | 6/1991 | Robertson . |
| 5,043,704 | 8/1991 | Blakeney . |
| 5,045,387 | 9/1991 | Schmalz . |
| 5,062,839 | 11/1991 | Anderson . |
| 5,074,854 | 12/1991 | Davis . |
| 5,087,255 | 2/1992 | Sims . |
| 5,102,668 | 4/1992 | Eichel et al. . |
| 5,114,788 | 5/1992 | Nakagawa et al. . |
| 5,120,598 | 6/1992 | Robeson et al. . |
| 5,123,411 | 6/1992 | Noziri . |
| 5,128,193 | 7/1992 | Anapol et al. . |
| 5,130,073 | 7/1992 | Meirowitz et al. . |
| 5,175,050 | 12/1992 | Meirowitz et al. . |
| 5,178,139 | 1/1993 | Angelillo et al. . |
| 5,192,606 | 3/1993 | Proxmire et al. . |
| 5,197,958 | 3/1993 | Howell . |
| 5,236,430 | 8/1993 | Bridges . |
| 5,244,695 | 9/1993 | Davidowich et al. . |
| 5,246,433 | 9/1993 | Hasse et al. . |
| 5,254,399 | 10/1993 | Oku et al. . |
| 5,264,269 | 11/1993 | Kakiuchi et al. . |
| 5,291,617 | 3/1994 | Moretz et al. . |
| 5,330,457 | 7/1994 | Cohen . |
| 5,334,177 | 8/1994 | Cohen . |
| 5,336,552 | 8/1994 | Strack et al. . |
| 5,342,343 | 8/1994 | Kitaoka et al. . |
| 5,364,382 | 11/1994 | Latimer et al. . |
| 5,429,629 | 7/1995 | Latimer et al. ............ 604/378 |

OTHER PUBLICATIONS

PPG Industries, Inc., Material Safety Data Sheet, "ALUBRASOFT™77–N". Last revised Mar. 8, 1993.

PPG Industries, Inc., Material Safety Data Sheet, "LAROSOL ASR". Last revised Jan. 26, 1993.

PPG Industries, Inc., Material Safety Data Sheet, "JORDAPON® CI POWDER". Last Revised Jul. 15, 1993.

PPG Textile Products Catalogue, Jun. 1991, PPG Industries, Inc. Gurnee, Illinois.

"The World of Surface Science" by D. O. Shah, University of Florida, Chemical Engineering Education, Winter 1977, pp. 14–23 and p. 48.

ENHANCED WET SIGNAL RESPONSE IN ABSORBENT ARTICLES

FIELD OF THE INVENTION

The present invention is directed to a liner and separation layer combination for use in personal care absorbent articles. More specifically, the present invention is directed to a fibrous nonwoven web liner and a fibrous nonwoven separation layer which when combined in a personal care absorbent article yield an initial wet feel to indicate to the user that an insult has occurred and then, with the passage of a short period of time, provides a drier and more comfortable feel.

BACKGROUND OF THE INVENTION

A major objective in the development of personal care absorbent articles over the last decade has been the creation of products which provide a clean and dry feel. Most personal care absorbent articles including diapers, training pants, incontinence devices, sanitary napkins, bandages and the like employ a liner or body facing material which is adapted to be placed adjacent the wearer's skin. Using diapers as an example, originally diapers were very wet to the touch once they had been insulted due to the inability of the diaper to channel fluids away from the wearer's skin to areas in the interior of the diaper where the liquid could be bound up and retained. As diaper and other personal care product designs have advanced, such products have become increasingly more effective at channeling fluids away from the wearer's skin and thereby creating a much drier feel. This has a number of benefits including, but not limited to, skin wellness, especially with diaper rash, and improved comfort to the wearer.

In the area of infant and/or child care, one of the most recent advances has been the creation of training pants which are a cross or bridge between diapers and underwear for children. The purpose of training pants is to provide a transitional garment during the toilet training stage of a child's development. One aspect of such training is the realization by the child that he or she has wet themselves. Unfortunately, the developments of personal care absorbent articles such as diapers and training pants have become so advanced that when an insult takes place, the child will feel little or no prolonged discomfort due to the liner quickly drying back out. It may be desirable if such products as diapers, training pants and incontinence garments would initially, upon insult, feel wet or damp so as to alert the wearer and temporarily remind them of the fact that an insult has taken place. For a number of reasons, once the insult has taken place, it may not be practical or possible to change the soiled product. As a result, the wearer may have to wear the soiled product for some length of time. Consequently, once the initial signal of an accident has been given to the wearer, it would be desirable if the liner material would then revert to as dry a feeling as was possible so as to provide comfort to the wearer until such time as the product could be changed. There is therefore a need for a personal care absorbent article which would initially provide a "wet" feel to the wearer to indicate that an insult has taken place but which over time would provide the wearer with as dry a feel as is practically possible. The present invention is directed to such a product.

SUMMARY OF THE INVENTION

The present invention is directed to personal care absorbent articles with a combination of a liner and a separation material which upon initial insult has a high relative surface moisture value but then, within a short period of time, the relative surface moisture drops to a lower value so that long term the overall product should have a more comfortable feel. These personal care absorbent articles typically include a liquid permeable body side liner, a separation layer, an outer cover and an absorbent core disposed between the separation layer and the outer cover to form the article. The body side liner is made from a fibrous nonwoven web which is wettable and which maintains its wettability over repeated insults. To this end the liner may include a durable, wettable treatment which is typically a surfactant. The separation layer is also made from a fibrous nonwoven web and unlike the body side liner has a low wettability as demonstrated by the surface wettability drop test. The resultant article in a general embodiment can have a relative surface moisture value of 70 percent or greater at approximately one minute after insult and a relative surface moisture value of 55 percent or less at approximately ten minutes. In a more refined embodiment the resultant article can have a relative surface moisture value at one minute of 75 percent or greater and 50 percent or less at ten minutes. In a yet more refined embodiment the article can have a relative surface moisture value at one minute of 80 percent or greater and 40 percent or less at ten minutes after insult as described in the test procedure outlined below.

In a more specific embodiment, the body side liner comprises a fibrous polyolefin nonwoven web having a basis weight ranging between about 17 grams per square meter and 28 grams per square meter (gsm). The separation layer may comprise a bonded carded web made from a blend of bicomponent and polyester fibers having a basis weight of at least 20 gsm with no real upper limit and with a more specific range being from about 40 to about 170 gsm and with a still more specific range being between about 40 and 60 gsm. The outer cover may comprise a layer of polyolefin film attached to a layer of fibrous nonwoven web and the absorbent core may contain at least about 20 percent by weight superabsorbent based upon the total weight of the absorbent core. The personal care absorbent article of the present invention has a wide variety of applications including, but not limited to, use in the form of a training pant, diaper or incontinence garment.

DETAILED DESCRIPTION OF THE INVENTION

The present invention is directed to a personal care absorbent article such as, for example, a training pant with a combination liner and separation layer for use as a child toilet training aid. The liner material of the present invention also can be used in other products and applications where a material is needed which when first insulted feels wet to the touch but, in a short period of time, again feels dry. Consequently, another use would be as a liner/separation material for other personal care absorbent articles including, but not limited to, diapers and incontinence garments.

Figure 1:
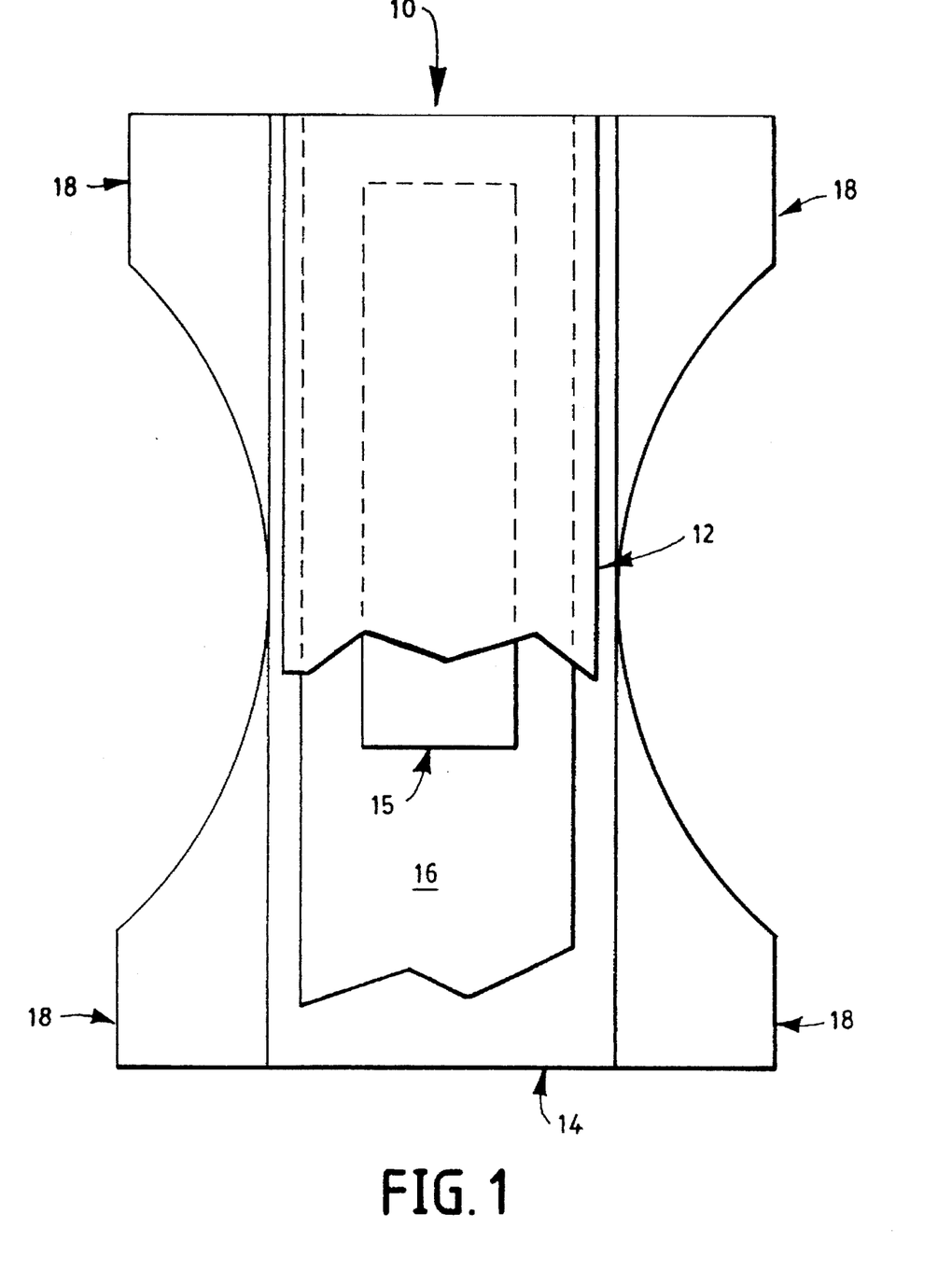
FIG. 1 is a partial cut-away top plan view of a personal care absorbent article, in this case, a training pant according to the present invention.

Personal care absorbent articles include such items as diapers, training pants, sanitary napkins, incontinence garments, bandages and the like. Referring to FIG. 1, in their most basic design all such articles 10 typically include a body side liner 12, an outer cover 14, a separation layer 15, and an absorbent core 16 disposed between the separation layer 15 and the outer cover 14. Generally, the body side liner 12 and the outer cover 14 are sealed to one another about their peripheries so as to encapsulate both the separation layer 15 and the absorbent core 16 and thus make it possible to entrap and retain any fluids contained within the absorbent core 16. Optionally the separation layer 15 may be adhesively attached to the liner 12 as well as the to the absorbent core 16.

The body side liner 12 of the present invention should have a continued hydrophilicity which is able to withstand multiple insults of liquid including such body fluids as urine. As a result, if the liner is not inherently wettable, it must be made to be so. Most thermoplastic synthetic fibers do not inherently meet this criterion. Thus they must be treated to make them more wettable. Consequently, wetting agents/ surfactants may be added either internally such as with siloxane during the fiber formation process, or externally as a post treatment either to the fibers and/or the resultant web as with anionic or nonionic surfactants including fluorocarbons. Such wetting agents/surfactants as well as their use are well known and need not be described here in detail.

As shown by the test data below, not all fiber treatments, typically referred to as surfactant treatments, are sufficiently durable. Many personal care absorbent products such as diapers are subjected to multiple insults during their use. Fugitive surfactants as the name implies tend to wash off the fibers with each insult and, as a result, the liner will become increasingly more hydrophobic. If the liner is to give a wet signal to the wearer on not only the first but also subsequent insults, this cannot occur. Consequently, once the web/liner has been formed, it is treated with a hydrophilic treatment which at least partially surrounds the exterior surfaces of the fibers. Conventional liner materials, such as surfactant treated polypropylene nonwoven webs, take in fluids very quickly and rapidly transfer the fluids to the underlying components. As a result, within a very short time, the liner feels dry to the user. The present invention moves away from this type of structure by providing a liner/separation layer combination which provides the exact opposite feel. The liner/separation layer combination of the present invention is capable of providing an initial wet signal which in a short period of time reverts to a dry feel. By using a durable hydrophilic finish on the liner and a more hydrophobic separation layer, the relative surface moisture can be maintained at a higher level for a longer period of time. This is accomplished by way of the present invention. As is shown by the test data below, when plotting wetness versus time, with the treatments, liners and separation materials of the present invention, higher wetness values are extended over a longer initial period of time while still having the liner ultimately return to an acceptable level of dryness in a reasonable period of time.

The body side liner 12 of the present invention comprises a web of material which is made from a plurality of fibers which are woven or nonwoven. Fibrous nonwoven webs have traditionally been found to work particularly well as the liner material for the present invention. Examples of such webs include, but are not limited to, spunbond webs, meltblown webs, bonded carded webs, air laid webs, wet laid webs, solution spun webs and generally any fibrous nonwoven web which has sufficient strength to be used as a liner for personal care absorbent articles.

The fibers can be any type of fiber, such as a short staple fiber or longer more continuous fibers as are found, for example, in meltblown and spunbond webs. The fibers can be natural or synthetic. Polyolefins, polyesters, cellulosics, polyacetates, and polyacrylate thermoplastics are some examples of polymers from which the fibers can be formed. In addition, it is possible to make fibers from homopolymers, copolymers, and blends of such polymers. It is also possible to form fibrous webs from blends of both synthetic fibers and natural fibers. Furthermore, the fibers may be hydrophilic by nature or they may be treated to be such.

The fibers themselves may have a variety of cross-sectional constructions including, but not limited to, solid, hollow, round, or irregular shapes such as bilobal, trilobal, and "x-shaped." The fibers also may be multiconstituent and/or multicomponent fibers. For example, biconstituent and bicomponent fibers work particularly well for bonding the fibrous web together. This is because such fibers typically have a lower melting point component which is used for heat bonding and a higher melting component which adds strength and resiliency to the fibers. Generally, the fibers will have average diameters which range between about 12 and about 45 microns.

In order to provide sufficient in-use-strength, the fibrous web will most typically require additional bonding. Fibrous woven webs oftentimes have sufficient strength due to the weaving pattern used to form the web. Nonwoven webs, on the other hand, even with carding, have a relatively random fiber pattern or orientation. Consequently, such webs may require additional levels of fiber entanglement or bonding, collectively referred to as "bonding." Examples of bonding methods or techniques include, but are not limited to, hydroentangling, needling, stitching, heat bonding, adhesive bonding, and ultrasonic bonding. When the fibers forming all or a portion of the web are thermoplastic in nature, heat and ultrasonic bonding have been found to work particularly well. When bicomponent fibers are being used and/or a more lofty web is desired, through air bonding works well. When higher strengths are required, point bonding is advantageous. Point bonding can be accomplished using, for example, ultrasonic bonding equipment or heated and patterned bonding rolls.

Nonwoven materials such as carded webs and spunbonded webs have been used as the body side liners in absorbent products. Specifically, porous liner structures have been employed to allow liquid to rapidly pass through them and to help keep the body skin separated from the wetted absorbent pad underneath the liner. In addition, other layers of material, such as those constructed with thick, lofty fabric structures, have been interposed between the liner and absorbent pad for the purpose of reducing wet back.

The present invention uses a separation layer composed of a lofty fibrous nonwoven web which is particularly well-suited for use in personal care absorbent articles including, but not limited to, diapers, training pants, incontinence garments, sanitary napkins, bandages and the like. A common problem with many of these products and their designs is the fact that they will not accept rapid and/or multiple insults of body fluids or exudates such as urine in a sufficiently short period of time without leaking. In an attempt to overcome this problem, many product designs include some sort of additional layer between the body side liner and the absorbent core to act as a dash pot of sorts to temporarily absorb, hold and then discharge the particular body exudate taken in from the liner. The present invention relates to a lofty fibrous nonwoven web which has been specifically designed and, which when incorporated into a personal care absorbent article or product that contains a body side liner that has a durable hydrophilic finish, provides an effective means for temporarily storing and then distributing body exudates while maintaining an initial wet signal. This material is referred to as the separation layer 15.

The separation layer 15 is most typically placed between and in contact with the body side liner 12 and the absorbent core 16 though other additional layers may be incorporated between the separation layer 15 and the absorbent core 16 or between the separation layer 15 and the liner 12 if so desired. To further enhance fluid transfer, it is desirable that the fibrous nonwoven separation layer be attached to the layers directly above and below its exterior surfaces. To this end, suitable attachment means include, but are not limited to, adhesives (water-based, solvent-based and thermal based adhesives), thermal bonding, ultrasonic bonding and needling as well as combinations of the foregoing or other appropriate attachment means.

The processes used to form the fibrous nonwoven web separation layer 15 include those which will result in a material which, as further described below, is very lofty and open in nature. Suitable processes include, but are not limited to, airlaying, spunbonding and bonded carded web formation processes. Spunbond nonwoven webs are made from fibers which are formed by extruding a molten thermoplastic material as filaments from a plurality of fine, usually circular, capillaries in a spinneret with the diameter of the extruded filaments then being rapidly reduced, for example, by non-eductive or eductive fluid-drawing or other well known spunbonding mechanisms. The production of spunbonded nonwoven webs is illustrated in patents such as Appel, et al., U.S. Pat. No. 4,340,563; Matsuki, et al., U.S. Pat. No. 3,802,817; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent Number 803,714, all of which are incorporated herein by reference in their entirety.

The spunbond process also can be used to form bicomponent spunbond nonwoven webs as, for example, from side-by-side polyethylene/polypropylene spunbond bicomponent fibers. The process for forming such fibers and resultant webs includes using a pair of extruders for separately supplying both the polyethylene and the polypropylene to a bicomponent spinneret. Spinnerets for producing bicomponent fibers are well known in the art and thus are not described herein in detail. In general, the spinneret includes a housing containing a spin pack which includes a plurality of plates having a pattern of openings arranged to create flow paths for directing the high melting and low melting polymers to each fiber-forming opening in the spinneret. The spinneret has openings arranged in one or more rows and the openings form a downwardly extending curtain of fibers when the polymers are extruded through the spinneret. As the curtain of fibers exit the spinneret, they are contacted by a quenching gas which at least partially quenches the fibers and develops a latent helical crimp in the extending fibers. Oftentimes the quenching air will be directed substantially perpendicularly to the length of the fibers at a velocity of from about 30 to about 120 meters per minute at a temperature between about 7° and about 32° C.

A fiber draw unit or aspirator is positioned below the quenching gas to receive the quenched fibers. Fiber draw units or aspirators for use in meltspinning polymers are well known in the art. Exemplary fiber draw units suitable for use in the process include linear fiber aspirators of the type shown in U.S. Pat. No. 3,802,817 to Matsuki et al. and eductive guns of the type shown in the U.S. Pat. Nos. 3,692,618 to Dorshner et al. and U.S. Pat. No. 3,423,266 to Davies et al. The fiber draw unit in general has an elongated passage through which the fibers are drawn by aspirating gas. The aspirating gas may be any gas, such as air that does not adversely interact with the polymers of the fibers. The aspirating gas can be heated as the aspirating gas draws the quenched fibers and heats the fibers to a temperature that is required to activate the latent crimps therein. The temperature required to activate the latent crimping within the fibers will range from about 43° C. to a maximum of less than the melting point of the low melting component polymer which, in this case, is the polyethylene. Generally, a higher air temperature produces a higher number of crimps.

The drawn and crimped fibers are deposited onto a continuous forming surface in a random manner, generally assisted by a vacuum device placed underneath the forming surface. The purpose of the vacuum is to eliminate the undesirable scattering of the fibers and to guide the fibers onto the forming surface to form a uniform unbonded web of bicomponent fibers. If desired, the resultant web can be lightly compressed by a compression roller before the web is subjected to a bonding process.

To bond the bicomponent spunbonded web a through-air bonder is used. Such through-air bonders are well known in the art and therefore need not be described in detail. In the through-air bonder, a flow of heated air is applied through the web to heat the web to a temperature above the melting point of the lower melting point component of the bicomponent fibers but below the melting point of the higher melting point component. Upon heating, the lower melting polymer portion of the web fibers are melted and the melted portions of the fibers adhere to adjacent fibers at the crossover points while the higher melting polymer portions of the fibers tend to maintain the physical and dimensional integrity of the web. For more information on forming bicomponent spunbond webs see U.S. Pat. No. 5,336,552 to Strack et al. which is incorporated herein by reference in its entirety.

Separation layers according to the present invention also can be made from bonded carded webs. Bonded carded webs are made from staple fibers which are usually purchased in bales. The bales are placed in a picker which separates the fibers. Next, the fibers are sent through a combing or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed through the web and then activated, usually by heating the web and adhesive with hot air. Another bonding method is pattern bonding wherein heated calender rolls or ultrasonic bonding equipment is used to bond the fibers together, usually in a localized bond pattern though the web can be bonded across its entire surface if so desired. The best method though, when using bicomponent staple fibers is to use a through-air bonder such as is described above with respect to the bicomponent spunbond web formation process in order to maintain the lofty and open nature of the resultant fibrous nonwoven web. In through-air bonding, heated air is forced through the web to melt and bond together the fibers at their crossover points. Typically the unbonded web is supported on a forming wire or drum. In addition a vacuum may be pulled through the web if so desired to further contain the fibrous web during the bonding process. Such through-air bonding processes are well known and therefore needs not be described herein in detail.

In order to form a fibrous nonwoven web separation layer with the parameters outlined below, at least a portion of the fibers forming the web must be made from polymers which are heat bondable. By heat bondable it is meant that the randomly deposited fibers forming the nonwoven web can be subjected to heat of a sufficient degree that the fibers will adhere to one another at the fiber cross over points due to the melting or partial softening of the polymer forming the heat bondable fibers. Suitable polymers for forming such heat bondable fibers are permanently fusible typically referred to as being thermoplastic. Examples of suitable thermoplastic polymers include, but are not limited to, polyolefins, polyesters, polyamides, rayon, orlon, acetates and polyvinyl alcohol as well as homopolymers, copolymers and blends.

When forming bonded carded webs, typical staple fiber lengths will range between about 38 and about 51 millimeters, though lengths outside this range also may be used. For example, airlaying typically involves using fibers with lengths in the range of about 6 to about 19 millimeters. Fiber diameters will be governed by the surface area to void volume parameters set forth below. Typically the fiber diameters will range between about 12 and about 45 microns with the target range being between about 19 and about 35 microns.

In order to achieve the lofty open structure of the separation layer portion of the present invention, it is desirable that the fibers be crimped. Crimping can be imparted both mechanically and chemically thereby forming both zig zag or saw tooth and helically or spirally crimped fibers. Fiber cross-sections may be either circular or non-circular including bilobal, trilobal, and X-shaped cross-sections. The fibers may be solid or hollow. In addition they may be made from a single fiber polymer or from multiple polymers such as is commonly found in biconstitutent and bi- or multicomponent fibers. When using bicomponent fibers, fiber cross-sections may include, for example, sheath/core, side-by-side and islands-in-the-sea cross-sections. Suitable bicomponent fibers include, whether in staple fiber or more continuous spunbond form, polyethylene/polypropylene and polyethylene/polyester fibers. The fibrous nonwoven web according to the present invention may be made entirely from bicomponent fibers or it may be made from a blend of bicomponent fibers and other fibers such as single component fibers including polyolefins such as polypropylene, polyesters, nylons and rayons. Generally, the fibrous nonwoven web separation layer according to the present invention will include at least 40% by weight, based upon the total weight of the web, bicomponent fibers. Such bicomponent fibers will typically have a fiber diameter equal to or greater than 16 microns.

The resultant fibrous nonwoven web will generally be a homogenous blend of whatever type fiber or fibers are chosen. It is also possible, however, to form multilayer structures provided they meet the parameters set forth with respect to the present invention.

The separation layer 15 of the present invention has been designed based upon a specific set of parameters. These parameters include basis weight, void volume, permeability, surface area per void volume, and hydrophilicity. The basis weight of the separation layer according to the present invention will be at least 20 grams per square meter with no real upper limit and with the target range being from about 40 to about 170 grams per square meter. The void volume of the fibrous nonwoven web is a measure of how much air space there is in the structure. The void volume is measured at 68.9 pascals and will range from about 17 to about 117 cubic centimeters per gram of web with the target range being from about 24 to about 80 cubic centimeters per gram of web. The permeability of the structure indicates the resistance of the material to the passing of a liquid through the structure of the material. When a fluid initially enters a separation layer structure, fluid movement is dominated by forced flow from the momentum of the insult velocity. Capillarity may not be significant in this flow regime as it may not have enough time to control the fluid path. Thus, fluid flow through the structure should be controlled by the permeability of the structure on the initial insult. A high permeability value indicates that it is relatively easy for a fluid to flow through the structure. Permeability for the materials according to the present invention will desirably range between about $5.0 \times 10^{-2}$ to about $1.0 \times 10^{-4}$ square centimeters (500 to 10,000 square microns).

The surface area per void volume with the void volume being measured at 68.9 pascals (0.01 pounds per square inch) pressure will range from about 15 to about 90 square centimeters per cubic centimeter. Permeability is the result of fluid having to travel over and around fiber surfaces when under forced flow in order to occupy the void spaces within the web. Surface area per void volume (SA/VV) indicates how closely together those fiber surfaces are located to each other. Thus, SA/VV can control the amount of permeability for a structure. A high SA/VV value indicates there is a large amount of surface area which is placed closely together. Increases in SA/VV can be achieved by using smaller fibers which increases the surface area per unit weight or by making the structure more dense which decreases the void volume per unit weight. When SA/VV is increased, permeability decreases since fluid is forced to travel over and around more surfaces to get through the structure. If the SA/VV becomes too high, then the permeability will be too low to allow easy fluid entry into and flow through the separation layer structure.

To ensure rapid intake of liquid, the overall structure must have some hydrophilic tendencies but if the amount of hydrophilic tendency becomes too great the liner will not be able to provide the necessary wet signal. The hydrophilic tendency of the separation layer can be determined by use of a surface wettability drop test as described under the test methods section. To provide the desired wet signal in combination with the durable hydrophilic liner, it is desirable that the separation layer have a drop test value equal to or greater than 6.

The absorbent core 16 which is disposed between the separation layer 15 and the outer cover 14 is used to absorb the main portion of the body fluids or other liquid delivered to it through the body side liner 12. Any of the currently available absorbent materials may be used to form the absorbent core. Examples of such materials include, but are not limited to, natural and synthetic wood pulp fluff fibers, hydrophilic thermoplastic fibers and superabsorbents.

Superabsorbents are water-swellable, water-soluble organic or inorganic materials capable, under the most favorable conditions, of absorbing at least about 20 times their weight and, more desirably, at least about 30 times their weight in an aqueous solution containing 0.9 weight percent sodium chloride. Organic materials suitable for use as superabsorbent materials in conjunction with the present invention can include natural materials such as agar, pectin, guar gum, and the like; as well as synthetic materials, such as synthetic hydrogel polymers. Such hydrogel polymers include, for example, alkali metal salts of polyacrylic acids, polyacrylamides, polyvinyl alcohol, ethylene maleic anhydride copolymers, polyvinyl ethers, methyl cellulose, carboxymethyl cellulose, hydroxypropylcellulose; and polymers and copolymers of vinyl sulfonic acid, polyacrylates, polyacrylamides, polyvinylpyrrolidone, and the like. Other suitable polymers include hydrolyzed acrylonitrile grafted starch, acrylic acid grafted starch, and isobutylene maleic anhydride polymers and mixtures thereof. The hydrogel polymers are preferably lightly crosslinked to render the materials substantially water insoluble. Crosslinking may, for example, be accomplished by irradiation or by covalent, ionic, van der Waals, or hydrogen bonding. The superabsorbent materials may be in any form suitable for use in absorbent composites including particles, fibers, flakes, spheres, and the like.

Such superabsorbents are usually available in particle sizes ranging from about 20 to about 1000 microns. The absorbent core 16 can contain from 0 to 100 percent superabsorbent by weight based upon the total weight of the absorbent core.

The outer cover 14 of the present invention has the purpose of retaining any exuded body fluids or other liquids within the absorbent core of the personal care absorbent product. Plastic films and/or nonwovens and/or film/nonwoven laminates can be used to form the outer covers. Thermoplastic polymers including, but not limited to, polyolefins have been found to work particularly well as the forming material for both film and nonwoven outer covers. If desired, the outer cover may be made breathable through the use of breathable plastic films and/or through the use of aperturing.

Depending upon the design of the particular personal care absorbent product, other components also may be included. For example, referring again to FIG. 1, if the personal care absorbent product 10 is a training pant, it also may include elastic side panels 18. The product also may include (not shown) such items as fluid containment flaps, fastening devices and other layers of liquid transfer or retention material. See for example U.S. Pat. No. 5,192,606 to Proxmire et al. which is incorporated herein by reference in its entirety.

Having thus described the invention in detail, several samples of the present invention were prepared and tested using the EDANA strike through test, surface wettability drop test and relative surface moisture test. The test procedures and examples are set forth below. In addition, test procedures are also set forth with respect to the calculation of basis weight, density, surface area per void volume and permeability.

TEST METHODS

BASIS WEIGHT

The basis weights for each of the samples was determined in accordance with Federal Test Method 191A/5041. Sample sizes were 5 inches by 5 inches (12.7 centimeters by 12.7 centimeters) and a total of 3 samples were weighed and then averaged for each material. The values reported are for the average.

BULK (THICKNESS)

Bulk which is a measure of thickness was measured using an INSTRON or SINTECH tensile tester to measure the resisting force as a material was compressed between a movable platen and a fixed base at a constant rate using a certain amount of force and subsequently releasing the force at the same rate. Preferably pressure, or force, and the platen pressure are recorded. If only force is recorded, pressure is calculated using the equation:

$$P_{reading} = \frac{F \times 10,000 \text{ cm}^2/\text{m}^2}{A_p}$$

where:

$P_{reading}$ = pressure reading from the SINTECH or INSTRON in pascals

F = force pushing back on the platen in pascals $A_p$ = area of the platen in square centimeters (19.02 cm$^2$)

In performing the measurements, the base of the apparatus must be larger in size that the platen. Zero height between platen and base distance was set by bringing the platen down until it barely touched the base. The platen was then raised to the desired initial height from zero distance. The initial platen position must be greater than the initial thickness of the material so that the test starts out at zero pressure on the sample. The material can be the same size as the platen or larger.

A 4.92 centimeter diameter circular platen was used to compress materials against the fixed base at a rate of 5.00 mm/minute up to a maximum load of 13,790 pascals (2.0 psi). The platen was then returned at the same rate to the initial starting position. The initial starting position for the platen was 13 millimeters from the base. Material samples were cut to 10.16 centimeter square shapes and tested in the center of the samples. Force and position data were recorded every 0.01 minutes or every 0.5 millimeters. Three samples were run for each material and averaged. The values reported are for the averages.

Suitable equipment for this test could include

Compression Tester:

INSTRON model 6021 with compression test software and 1 kN load cell made by Instron of Bucks, England.

Balance:

Mettler model PM4600 of Highstown, N.J.

To measure bulk or thickness, the following equation was used:

$$\text{Bulk(thickness)} = x_o - x$$

where:

$x_o$ = distance of initial platen position from the base in millimeters x = platen position from initial position in millimeters at a specific pressure, in this case 68.9 pascals Thus all bulk values reported were for samples while under a load or pressure of 68.9 pascals.

DENSITY

The density of the materials was calculated by dividing the weight of a sample in grams per square meter (gsm) by the bulk of the sample in millimeters (mm) at 68.9 pascals and multiplying the result by 0.001 to convert the value to grams per cubic centimeter (g/cc). A total of three samples were evaluated and averaged for the density values reported herein.

SURFACE AREA PER VOID VOLUME (SA/VV)

Surface area per void volume was calculated by determining the fiber surface area in square centimeters per one gram of sample and dividing that by the void volume of the sample which is simply the inverse of density measured at 68.9 pascals. Surface area per void volume gives an indication of how much resistance liquid encounters as it passes through the web structure. SA/VV can be thought of as being similar to the mesh size of a screen. A large SA/VV means that the wires of the screen are closer together thus making the holes in the screen smaller. As the holes get smaller, it becomes more difficult for liquid to pass through the screen.

For purposes of the present invention it is desirable to generate webs with low SA/VV values so that liquid can pass through the web with relative ease. The data generated in conjunction with the Examples was based upon an average of three samples per Example.

The surface area of the fibers in a one gram sample of web material was calculated using the following equation:

Surface Area (SA) per gram of web=3363×{(Fiber 1 Denier/Fiber 1 Density)$^{0.5}$×(1/Fiber 1 Denier)×Fiber 1 Weight % of Web}+ 3363×{(Fiber 2 Denier/Fiber 2 Density)$^{0.5}$ ×(1/Fiber 2 Denier)×Fiber 2 Weight % of Web}.

Surface Area per Void Volume (SA/VV) is then calculated by dividing the SA by the VV or, as stated above, multiplying by the density of the web as follows:

SA/VV=SA (cm$^2$/g)×Density of Web (g/cm$^3$)=SA/VV in cm$^2$/cm$^3$.

To illustrate the above calculations, the SA/VV for the Separation Layer 1 in Example 2 is set forth below.

The fibrous nonwoven web Separation Layer 1 in Example 2 had the following properties:

Web Density=0.0223 g/cc

Fiber 1 Diameter=19.1 microns (μ)

Fiber 1 Density=1.165 g/cc

Fiber 1 Weight % of Web=0.60

Fiber 2 Diameter=24.8 microns

Fiber 2 Density=1.38 g/cc

Fiber 2 Weight % of Web=0.40

SA={3363×(3.0/1.165)$^{0.5}$×(1/3.0)×0.60}+{3363 ×(6.0/1.38)$^{0.5}$×(1/6.0×0.40}=1546.8 cm$^2$/g

SA/VV=SA×Density of Web=1546.8 cm$^2$/g ×0.0223 g/cm$^3$=34.5 cm$^2$/cm$^3$.

PERMEABILITY

Permeability (K) was calculated using the following equation:

$$K=0.075 \times R^2 \times (1-E) \times (E/(1-E))^{2.5}$$

where

R=average fiber radius and E=web openness.

R was calculated as follows:

R={(4×(Weight % fiber 1)/(Density of fiber 1)×(Specific surface area of the web)×0.0001)+(4 ×(Weight % fiber 2)/(Density of fiber 2)×(Specific surface area of the web)×0.0001)}/2.

The Specific Surface Area (SSA) of the web was calculated as follows:

SSA={4×(Weight % of fiber 1)/((Micron diameter of fiber 1)×(Density of fiber 1)×0.0001) }+{4 ×(Weight % of fiber 2)/((Micron diameter of fiber 2) ×(Density of fiber 2)×0.0001)}.

E was calculated as follows:

E=1−{(Web density)×(Weight % of fiber 1)/(Density of fiber 1)−(Web density)×(Weight % of fiber 2)/(Density of fiber 2)}.

If more than two fibers are used, the equations can be expanded. This calculation assumes cylindrical fibers and that the web is at 100% saturation.

To demonstrate the use of the above equations, the permeability value was calculated for Separation Layer 1 in Example 2.

The fibrous nonwoven web of Separation Layer 1 had the following properties:

Web Density=0.0223 g/cc

Fiber 1 Diameter=19.1 microns (μ)

Fiber 1 Density=1.165 g/cc

Fiber 1 Weight % of Web=0.60

Fiber 2 Diameter=24.8 microns

Fiber 2 Density=1.38 g/cc

Fiber 2 Weight % of Web=0.40

Specific Surface Area (SSA) of the Web={4×0.60/(19.1× 1,165 ×0.0001)}+{4×0.40/(24.8×1.38×0.0001)}= 1546.09 cm$^2$/g R={(4×0.60/(1,165×1546.09×0.0001)+(4×0.40/(1.38 ×1546.09×0.0001)}/2=10.4 microns

E=1−{(0.0223 ×0.60/1,165)−(0.0223 ×0.40/1.38)}= 0.98205

Therefore, the permeability (K)=0.075×10.4$^2$ ×(1 −0.98205)×(0.98205/(1−0.98205))$^{2.5}$ =3228 μ$^2$

LIQUID STRIKE-THROUGH TEST

The Liquid Strike-Through time was measured by using EDANA test procedure 150.1-90. A LISTER type timer/dispenser manufactured by Lenzing Aktiengesellschaft, Division Lenzig Technik, A-4860 Lenzing, Austria was used. The simulated Urine test fluid was replaced with certified blood bank saline (Catalogue No. B3158-1) from the Baxter Healthcare Corporation, Scientific Products Division, McGaw Park, Ill. The saline solution was a stabilized isotonic 0.9% saline solution containing no preservatives. The saline solution was at ambient temperature −22° to 23° C. Three insults were run over the same sample to simulate repeated wash off of the surfactant due to repeated insults of the material. After each insult the sample was allowed to air dry for a minimum of one (1) hour before the next insult was performed.

SURFACE WETTABILITY DROP TEST

SCOPE

This procedure describes a test to assess the surface wettability of fibrous nonwoven webs.

SUMMARY

Fibrous nonwoven webs such as the separation layer of the present invention material perform best if the surface of the fibers are more hydrophobic. Current wet-out tests such as the float or basket sink tests are not adequate because they either give subjective measurements or they distort the surface of the sample. A more discretionary test is needed to allow small changes in fiber wettability to be measured.

The test described in this procedure used a simple eye dropper to place liquid on the surface of a piece of separation material. In this procedure, a sample 23 centimeter (cm) in the machine direction (MD) × 23 cm in the cross-machine direction (CD) was cut and ten separate drops of liquid were placed on the sample surface. The number of drops on the surface were then counted and recorded. A count of 0 indicated a highly wettable surface, a count of 10 indicated a highly non wettable surface. A count between 0 and 10 indicates various degrees of wettability.

EQUIPMENT & MATERIALS b 1. Plastic eye dropper, Fisherbrand transfer pipets disposable polyethylene Cat. no. 13-711-5A from Fisher Scientific.

2. Distilled or deionized water.

3. Erlenmeyer Flask, 250 ml.

SAMPLE PREPARATION

1. Cut sample to 23 cm MD×23 cm CD dimension.

2. Fill Erlenmeyer flask with 200 ml of distilled/deionized water.

TESTING PROCEDURE

1. Place sample on flat nonporous surface, such as layer of plexiglass or a lab bench top.
2. Using polyethylene pipet, draw the water into the pipet.
3. Starting from the upper left end of the sample, hold the pipet slightly above the surface of the sample (about one centimeter).
4. Squeeze the bulb of the pipet so that a drop of water begins to form at the tip of the pipet.
5. When the drop of water is ready to fall from the tip of the pipet, gently position the drop on the surface of the sample and quickly remove the tip of the pipet so the drop remains on the surface of the sample.
6. Move over approximately 2 cm and place a second drop onto the surface of the sample.
7. Continue moving across the CD direction of the sample until a total of ten drops have been placed on the sample surface. The total time for applying all ten drops should be approximately 10 seconds.
8. Immediately count from left to right the number of drops that are still above, even if only partially, the horizontal plane of the sample. Counting of the drops should take no more than an additional five seconds.
9. Record this number.
10. The test is repeated a minimum of 5 times and the number of drops are averaged for the reported values.

RESULTS

1. A count of zero drops indicates a highly wettable surface.
2. A count greater than zero drops indicates decreasing wettability with higher numbers being more non wettable than lower numbers.
3. A count of ten drops indicates a highly non wettable surface.

RELATIVE SURFACE MOISTURE TEST (SDME)

The relative surface moisture in the liner and overall product was calculated from measurements made using a Surface Dryness Measuring Equipment apparatus manufactured by Hoechst Atkiengesellschaft of West Germany. A detailed description of this type of equipment and its operation can be found in U.S. Pat. No. 4,924,084 to Lask et al. which is incorporated herein by reference in its entirety. The equipment for this apparatus included a Strip chart recorder from the Linear Instrument Corporation of Reno, Nev. (Model 1201). The chart recorder recorded moisture readings from an optical light sensor which in turn was connected to a DC power source. Prior to the conductance of testing, the equipment was turned on and allowed to warm up for a minimum of 45 minutes.

To test each sample, each sample was placed on top of a plexiglass plate measuring 9 centimeters (cm) in width and 43 cm in length. In order to normalize the moisture values for each sample, a dry reading and a wet reading were both obtained in addition to the actual wetness curve which was generated over a preselected time interval which in this case was 10 minutes. A total of three samples were run for each material and averaged. The reported values or for the averages.

To obtain a dry reading and thus a lower limit on the graph, the sensor was placed over the top of the sample with the longitudinal axis of the sensor being perpendicular to the longitudinal axis of the sample and with the ends of the optical light sensor extending equidistant over both side edges of the sample. The sample was positioned with the liner side adjacent the light sensor and the back sheet facing the plexiglass support. The chart pen was then activated by switching the recorder from stand-by to record and the pen was zeroed over the 20 grid mark location. The recorder was then returned to stand-by and the detector was removed from the sample.

Next a stainless steel ring having a 6 centimeter inner diameter, a height of 4 centimeters and a weight of approximately 326 grams was centered over the longitudinal and transverse center of the sample in the same location as the dry reading was taken. Into the center of the steel ring there was poured 80 milliliters of certified blood bank saline (Catalogue No. B3158-1) from the Baxter Healthcare Corporation, Scientific Products Division, McGaw Park, Ill. The saline solution was a stabilized isotonic 0.9% saline solution containing no preservatives. The saline solution was at ambient temperature–22° to 23° C.

The 80 milliliters of saline solution was quickly poured into the ring and thus onto the liner side of the absorbent sample. Immediately after the saline solution was absorbed below the surface of the liner (no excess liquid standing on the liner), the stainless steel ring was removed and the optical light sensor was immediately placed on top of the sample in the same manner as described before and the chart recorder was switched from stand-by to record. The recorder was adjusted to a chart speed of 1 centimeter per minute and the test was allowed to run for a total of ten minutes. At the end of the ten minute interval, the chart pen was lifted and the chart was turned off by switching the chart to stand-by. Next, the ring was placed back on top of the sample in the same location as before and the sample was totally saturated by pouring an additional quantity of saline solution generally in an amount of about 100 milliliters so as to completely saturate the absorbent core. The amount of liquid in the pad after the second insult should be enough such that the weight of the sensor causes slight flow back of the liquid to the surface. The ring was then removed and the optical light sensor, whose optical sensing portion had been wiped free of any excess saline solution from the previous measurement, was placed in the same location on top of the sample in the same manner as described above. The chart was again switched from standby to record and the chart was either momentarily activated or the chart paper was moved back and forth so as to achieve a mark or location on the grid paper representing the total saturation measurement for the sample. Having done this, each sample then has a zero or dry value ($V_D$), a total saturation value ($V_S$) and a time dependent curve extending from the point of absorption of the initial 80 milliliters of saline solution to a point ten minutes later.

Following the collection of this data, the relative surface moisture values were calculated using the following equation:

$$V_R = \text{relative surface moisture (\%)} = \frac{V_T - V_D}{V_S - V_D} \times 100$$

where:

$V_T$ is the value on the curve at a given time.

$V_D$ is the value on the curve when the sample is dry.

$V_D$ equaled 20 for all examples tested.

$V_S$ is the value on the curve when the sample is saturated.

EXAMPLES

To demonstrate the present invention, a series of liner materials were made and treated with various surfactant treatments. These liner materials were then tested using the EDANA Liquid Strike-Through test to determine how quickly the surfactant would wash off the liner materials.

This information is presented in Example 1. Next two separation layers were produced and evaluated for their hydrophilicity/hydrophobicity using the Surface Wettability Drop test. This information is presented in Example 2. Once the characteristics of the liner and separation materials were determined, nine absorbent article designs were made and tested. The designs were incorporated into pad structures according to the invention and were tested using the Relative Surface Moisture test. This information is contained in Example 3.

EXAMPLE 1

In Example 1 three liner materials were tested for liner durability using the Edana Liquid Strike-Through Test outlined above. All three liners were made from the same fibrous nonwoven web with the difference being in the surfactant treatment on each of the liner materials. The liner was a 20.3 gram per square meter (gsm) polypropylene spunbond web having an average fiber diameter of 20 microns. The liner material was point bonded with an overall bond area of approximately 19 percent using a bond density of approximately 46 bond points per square centimeter. The individual bond points had an approximate surface area of 0.00413 square centimeters. The body side liners were treated with 2.1 percent by weight, based upon the total weight of the liner of the surfactants described below.

Liner 1 was treated with Triton X-102 surfactant which is a octylphenoxypolyethoxyethanol nonionic surfactant available from the Union Carbide Chemicals and Plastics Company, Inc. of Danbury, Conn. Liner 2 was treated with a blend of 70 weight percent Lubrizol 85870 surfactant and 30 weight percent Y12488 surfactant. Lubrizol 85870 surfactant is a succinic anhydride ethoxylated fatty amine salt surfactant available from Lubrizol Corp. of Wickliffe, Ohio. Y12488 surfactant is a polyalkeneoxide modified polydimethylsilicone nonionic surfactant produced by OSI Specialties Inc. of Tarrytown, N.Y. Liner 3 was treated with Ahcovel® Base N-62 liquid nonionic textile softener from ICI Americas, Inc. of Wilmington, Del. Ahcovel® textile softener is a blend of sorbitan monooleate (CAS 1338-43-8) and polyethoxylated hydrogenated castor oil (CAS 61788-85-0). Each of the liners was subjected to strike through testing with three successive insults of saline solution as outlined in the test procedure described above. A total of ten samples were tested for each liner material. In order to perform properly for the present invention it is desirable that the liner material have a durable finish so that it can endure multiple insults without the surfactant treatment washing off prematurely. The results are set forth in Table 1 below.

TABLE 1

| 5 ml INSULT TREATMENT | STRIKE THROUGH TIME | | |
|---|---|---|---|
| | 1st (seconds) | 2nd (seconds) | 3rd (seconds) |
| Liner 1 | 2.83 | 8.92 | 12.11 |
| TRITON | 2.45 | 3.15 | 6.85 |
| | 2.41 | 4.30 | 11.16 |
| | 2.74 | 31.54 | 39.74 |
| | 2.84 | 12.25 | 24.33 |
| | 2.92 | 21.03 | 25.41 |
| | 2.33 | 7.19 | 11.66 |
| | 2.35 | 8.73 | 4.03 |
| | 2.52 | 119.57 | 6.41 |
| | 2.46 | 10.05 | 22.55 |
| AVERAGE | 2.59 | 22.67 | 16.43 |

TABLE 1-continued

| 5 ml INSULT TREATMENT | STRIKE THROUGH TIME | | |
|---|---|---|---|
| | 1st (seconds) | 2nd (seconds) | 3rd (seconds) |
| STANDARD DEV. | 0.21 | 33.29 | 10.67 |
| Liner 2 | | 1.85 | 2.1485 |
| LUBRIZOL/Y12488 | 2.24 | 2.30 | 2.16 |
| | 2.78 | 2.38 | 2.11 |
| | 3.07 | 2.60 | 2.02 |
| | 2.64 | 2.10 | 2.26 |
| | 2.81 | 2.65 | 2.51 |
| | 2.10 | 2.35 | 2.76 |
| | 2.04 | 3.00 | 2.26 |
| | 2.01 | 2.24 | 2.24 |
| | 2.63 | 2.39 | 2.25 |
| AVERAGE | 2.42 | 2.42 | 2.24 |
| STANDARD DEV. | 0.40 | 0.26 | 0.24 |
| Liner 3 | 2.40 | 2.37 | 2.92 |
| AHCOVEL | 2.54 | 2.50 | 2.76 |
| | 2.64 | 2.27 | 2.72 |
| | 2.89 | 2.39 | 2.86 |
| | 2.56 | 2.44 | 2.46 |
| | 2.40 | 2.34 | 2.53 |
| | 2.49 | 2.10 | 2.67 |
| | 2.24 | 2.30 | 2.91 |
| | 2.28 | 2.83 | 2.31 |
| | 2.53 | 2.65 | 2.46 |
| AVERAGE | 2.50 | 2.42 | 2.66 |
| STANDARD DEV. | 0.18 | 0.19 | 0.20 |

As can be seen from the data in Table 1, the insult time which is the time for the liner material to absorb the 5 cubic centimeters (cc) of saline solution increased dramatically for the Liner 1 material between the first and third insults. In contrast, Liner materials 2 and 3 maintained an insult time of five seconds or less even through the third insult. As will be demonstrated by the further testing below, these latter two liner materials when combined with an appropriate separation layer material provided an acceptable wetness signal indicator.

EXAMPLE 2

Another important feature of the present invention is the combination of a durable liner with a hydrophobic separation layer to yield an appropriate wetness signal. In Example 2, two separation layer materials were tested for their hydrophilicity according to the Surface Wettability Drop Test outlined above. Separation Layer 1 was a through-air bonded carded web made from a blend of 40 weight percent (based upon the total weight of the web) T-295 6 denier Polyester fibers and 60 weight percent (based upon the total weight of the web) of a T-256 3 denier Polyethylene sheath/ Polyester core bicomponent fiber. Both fibers are manufactured by the Hoechst Celanese Corporation. The T-256 fiber had a staple length of 38 mm and the T-295 fiber had a length of 51 mm. Both of the fibers are provided with a finish treatment by the manufacturer which was not removed.

Separation Layer 1 had a basis weight of 50.9 gsm, a bulk at 68.9 pascals of 2.29 millimeters (mm), a density at 68.9 pascals of 0.022 grams per cubic centimeter (g/cc), a void volume of 44.9 cc/g at 68.9 pascals, a SA/VV at 68.9 pascals of 34.5 $cm^2/cm^3$, a permeability of 3228 square microns and an average surface wettability drop test value of 8.2 drops.

Separation Layer 2 was made from a blend of 40 weight percent T-295 6 denier Polyester fibers and 60 weight percent of a ESC 3 denier Polyethylene sheath/ Polypropylene core bicomponent fiber. Both weight percents were based upon the total weight of the web. The polyester fiber was the same as that use in Separation Layer 1. The bicomponent fiber was obtained from the Chisso Corporation of Osaka, Japan. It, too, was treated with a finish by the manufacturer.

Separation Layer 2 had a basis weight of 52.9 gsm, a bulk at 68.9 pascals of 2.64 millimeters (mm), a density at 68.9 pascals of 0.020 grams per cubic centimeter (g/cc), a void volume of 49.9 cc/g at 68.9 pascals, a SA/VV at 68.9 pascals of 33.6 $cm^2/cm^3$, a permeability of 3477 square microns and an average surface wettability drop test value of 0.0 drops.

Both separation layers were subjected to the Surface Wettability Drop test and the results are set forth in Table 2 below. A drop value of 6 drops or greater is desirable for the present invention as it is an indication of a material which is sufficiently hydrophobic.

TABLE 2

| | SURFACE WETTABILITY DROP TEST RAW DATA | |
|---|---|---|
| Sample | Separation Layer 1 60% T-256 Bico 40% T-295 PET (number of drops) | Separation Layer 2 60% ESC Bico 40% T-295 PET (number of drops) |
| 1 | 9 | 0 |
| 2 | 7 | 0 |
| 3 | 8 | 0 |
| 4 | 8 | 0 |
| 5 | 10 | 0 |
| 6 | 8 | 0 |
| 7 | 6 | 0 |
| 8 | 9 | 0 |
| 9 | 8 | 0 |
| 10 | 9 | 0 |
| 11 | 8 | 0 |
| 12 | 9 | 0 |
| 13 | 7 | 0 |
| 14 | 8 | 0 |
| 15 | 8 | 0 |
| 16 | 9 | 0 |
| 17 | 9 | 0 |
| 18 | 10 | 0 |
| 19 | 7 | 0 |
| 20 | 8 | 0 |
| Total | 165 | 0 |
| Average | 8.25 | 0 |
| Std Dev. | 1.0 | 0 |

As can be seen from the data in Table 2, Separation Layer 1 had an average value of 8.25 drops which is acceptable for the present invention while Separation Layer 2 was too hydrophilic with an average value of 0 drops.

Example 3

In Example 3 nine different absorbent articles or systems were made and tested for relative surface moisture values. Since there were three liner materials (the same nonwoven with three different surfactant treatments) and two separation layers, the total number of combinations were six. In addition, the three liner materials were each made into absorbent articles without separation layers underneath to demonstrate the value of the separation layer as part of the present invention. Each of the absorbent articles used the same absorbent core and outer cover. The variable in each embodiment was the liner/separation layer combination. The actual combinations for each of the Systems are outline below.

System 1—Liner 3 and Separation Layer 1.
System 2—Liner 3 and Separation Layer 2.
System 3—Liner 2 and Separation Layer 1.
System 4—Liner 2 and Separation Layer 2.
System 5—Liner 1 and Separation Layer 1.
System 6—Liner 1 and Separation Layer 2.
System 7—Liner 3 only.
System 8—Liner 2 only.
System 9—Liner 1 only.

The test pads for each of the Systems had a length of approximately 38.1 cm and a width of 12.7 cm and curved inwardly along the longitudinal sides. The overall surface area of the pads was approximately 335 $cm^2$. All the test pads had the same outer cover including an interior layer of 18 micron thick polypropylene film adhesively laminated to an exterior layer of 27 grams per square meter (gsm) polypropylene spunbond web. The body side liner used in all examples was the previously described 20.3 gsm polypropylene spunbond web having an average fiber size of 20 microns. The absorbent core for each of the test pads had a total weight of 25 grams with 11 grams of Kimberly-Clark CR-254 wood pulp fluff and 14 grams of SAB 836 cross-linked polyacrylate particulate superabsorbent from Stockhausen of Greensboro, N.C. The wood pulp fluff and superabsorbent particles were mixed together to form the absorbent core and the core was wrapped with a 23.5 grams per square meter non-optically brightened wet strength tissue wrap sheet. The various Separation Layers outlined above were place between the body side liners and the absorbent cores. There was no adhesive or other attachment means to attach the layers of the test pads together or to seal their peripheries.

Each of the absorbent article test pads incorporating the various system combinations was evaluated for relative surface moisture using the test procedure described above. Initial and final values for each of the systems were obtained as well as values every 12 seconds over a ten minute period. The actual raw data for each of the systems is presented in Table 3 below and is also depicted graphically in FIG. 2 of the drawings.

TABLE 3

| | | Surface Dryness/Moisture Evaluation Testing Percent Relative Moisture | | | | | | | | |
|---|---|---|---|---|---|---|---|---|---|---|
| | | System 1 | System 2 | System 3 | System 4 | System 5 | System 6 | System 7 | System 8 | System 9 |
| Start | | 99% | 99% | 99% | 97% | 99% | 99% | 99% | 98% | 99% |
| | | 95% | 94% | 91% | 81% | 91% | 96% | 80% | 72% | 96% |
| | | 90% | 92% | 87% | 65% | 78% | 80% | 70% | 59% | 88% |
| | | 87% | 70% | 84% | 58% | 69% | 69% | 63% | 48% | 67% |
| | | 86% | 63% | 82% | 54% | 64% | 64% | 58% | 42% | 56% |

TABLE 3-continued

Surface Dryness/Moisture Evaluation Testing
Percent Relative Moisture

|  | System 1 | System 2 | System 3 | System 4 | System 5 | System 6 | System 7 | System 8 | System 9 |
|---|---|---|---|---|---|---|---|---|---|
| 1 MIN. | 86% | 59% | 81% | 51% | 60% | 60% | 54% | 37% | 50% |
|  | 85% | 56% | 79% | 49% | 58% | 57% | 50% | 32% | 46% |
|  | 85% | 54% | 77% | 48% | 55% | 54% | 47% | 28% | 43% |
|  | 84% | 52% | 76% | 46% | 52% | 52% | 43% | 24% | 39% |
|  | 83% | 51% | 75% | 45% | 49% | 49% | 41% | 21% | 37% |
| 2 MIN. | 83% | 50% | 74% | 43% | 47% | 47% | 39% | 19% | 35% |
|  | 82% | 49% | 73% | 42% | 46% | 44% | 37% | 19% | 33% |
|  | 82% | 48% | 72% | 41% | 43% | 43% | 35% | 17% | 32% |
|  | 81% | 48% | 70% | 40% | 41% | 41% | 34% | 17% | 32% |
|  | 80% | 47% | 69% | 39% | 40% | 39% | 32% | 16% | 32% |
| 3 MIN. | 80% | 46% | 69% | 38% | 39% | 37% | 30% | 16% | 31% |
|  | 79% | 46% | 67% | 37% | 37% | 35% | 30% | 15% | 31% |
|  | 78% | 45% | 66% | 36% | 36% | 34% | 28% | 15% | 31% |
|  | 77% | 44% | 66% | 35% | 35% | 33% | 27% | 15% | 31% |
|  | 77% | 44% | 64% | 35% | 34% | 32% | 26% | 15% | 31% |
| 4 MIN. | 76% | 44% | 64% | 33% | 34% | 31% | 26% | 15% | 31% |
|  | 76% | 43% | 62% | 33% | 33% | 29% | 26% | 15% | 31% |
|  | 75% | 43% | 61% | 31% | 33% | 29% | 26% | 15% | 31% |
|  | 74% | 43% | 60% | 31% | 32% | 28% | 25% | 15% | 31% |
|  | 73% | 42% | 59% | 29% | 32% | 27% | 24% | 15% | 31% |
| 5 MIN. | 73% | 42% | 57% | 29% | 31% | 27% | 24% | 15% | 31% |
|  | 72% | 41% | 56% | 28% | 31% | 27% | 24% | 15% | 31% |
|  | 71% | 41% | 55% | 27% | 30% | 27% | 24% | 15% | 32% |
|  | 70% | 40% | 54% | 27% | 30% | 26% | 24% | 15% | 32% |
|  | 69% | 40% | 53% | 26% | 30% | 26% | 24% | 15% | 32% |
| 6 MIN. | 68% | 39% | 51% | 25% | 30% | 26% | 24% | 15% | 32% |
|  | 67% | 39% | 50% | 25% | 29% | 26% | 24% | 15% | 32% |
|  | 66% | 39% | 48% | 24% | 29% | 26% | 24% | 15% | 32% |
|  | 65% | 38% | 47% | 24% | 29% | 25% | 24% | 13% | 32% |
|  | 64% | 38% | 46% | 23% | 29% | 25% | 24% | 15% | 32% |
| 7 MIN. | 63% | 37% | 45% | 23% | 29% | 25% | 24% | 15% | 32% |
|  | 62% | 36% | 43% | 23% | 29% | 26% | 24% | 15% | 32% |
|  | 61% | 36% | 42% | 23% | 29% | 25% | 24% | 15% | 32% |
|  | 61% | 36% | 41% | 22% | 29% | 25% | 24% | 15% | 32% |
|  | 59% | 35% | 41% | 22% | 28% | 25% | 24% | 15% | 32% |
| 8 MIN. | 59% | 35% | 40% | 22% | 28% | 25% | 24% | 15% | 32% |
|  | 57% | 35% | 39% | 22% | 28% | 25% | 24% | 15% | 32% |
|  | 56% | 34% | 38% | 22% | 28% | 25% | 24% | 15% | 32% |
|  | 55% | 33% | 36% | 22% | 28% | 25% | 24% | 15% | 32% |
|  | 54% | 33% | 36% | 22% | 28% | 26% | 24% | 15% | 32% |
| 9 MIN. | 53% | 32% | 35% | 22% | 28% | 26% | 23% | 15% | 32% |
|  | 52% | 32% | 34% | 22% | 28% | 26% | 23% | 15% | 32% |
|  | 51% | 32% | 33% | 22% | 28% | 26% | 23% | 15% | 32% |
|  | 50% | 32% | 32% | 22% | 28% | 25% | 22% | 15% | 32% |
|  | 49% | 32% | 32% | 22% | 28% | 25% | 22% | 15% | 32% |
| END | 48% | 32% | 31% | 22% | 28% | 25% | 22% | 15% | 32% |

Figure 2:
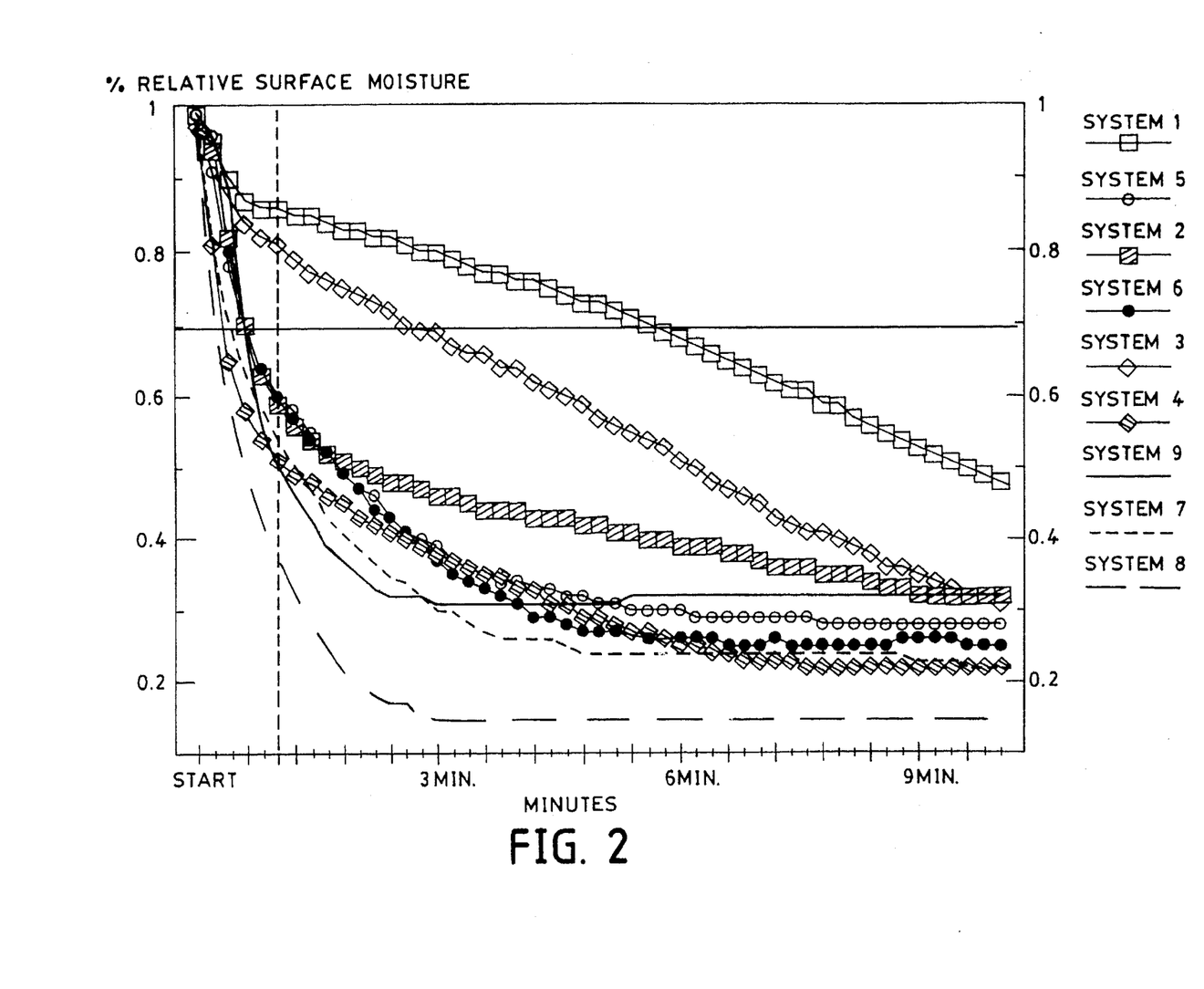
FIG. 2 is a graph showing relative surface moisture values over time for several personal care absorbent articles including the present invention.

As can be seen from the data in Table 3 and its depiction in FIG. 2 of the drawings, the test pads incorporating Systems 1 and 3 had the highest relative surface moisture readings at the one minute interval with respective percentages of 86 and 81 percent. These same absorbent articles had relative surface moisture values at ten minutes of 48 and 31 percent, respectively. Both Systems used Separation Layer 1 which was clearly the more hydrophobic of the two separation layer materials. It had an average drop test value of 8.25 whereas the other material had an average value of zero. System 1 used Liner 3 and System 3 used Liner 2 both of which had low average liquid strike through times on all three of the insults as shown by the data in Example 1. Consequently, these combinations of a durable wettable liner and a hydrophobic separation layer clearly gave the optimum "wet feel" at the one minute interval after initial insult while still drying out to an acceptable level after approximately ten minutes. This can be compared to Systems 7, 8 and 9 which had no separation layers. These Systems when incorporated into the test pads dried out very quickly as can be seen by their respective relative surface moisture values at one minute.

The test pads with Systems 2, 5 and 6 all yielded the same general results at the one minute interval (59%, 60% and 60% respectively) with these results being much lower than the values at one minute for the pads with Systems 1 and 3. Thus it would appear that the detrimental component in the System 2 pad was the hydrophilic Separation Layer 2 while with the System 5 pad it was the less durable liner (Liner 1). Finally, the pad with System 6 suffered from the combination of both the less durable liner (Liner 1) and the more hydrophilic separation layer (Separation Layer 2). As a result, it also dried out too quickly. Thus, Systems 2, 5 and 6 showed the ill effects of improper liner/separation layer combinations in that the resultant test pads again gave too dry a relative surface moisture reading at the one minute interval. In the same fashion, the pad with System 4 did not work well because, even though it had a durable liner (Liner 2), the separation layer was not sufficiently hydrophobic (Separation Layer 2) to yield in combination with the liner a relative surface moisture value of at least about 70 percent at one minute.

Thus in summary it can be seen that by properly selecting a combination of liner and separation layer in combination with an overall absorbent article product design, a resultant product can be designed which will yield an initial "wet feel" at approximately one minute but by approximately ten minutes will dry out to a much more acceptable level as shown by the relative surface value readings. Generally, the resultant product will have a relative surface moisture value at one minute after insult with 80 milliliters of stabilized isotonic 0.9 percent saline solution of approximately 70 percent or greater and a value at approximately ten minutes of approximately 55 percent or less. Depending upon the level of design, these one and ten minute values can be increased respectively to 75%(one minute)/50%(ten minutes), 80%/50% and 80%/40%.

Having thus described the invention in detail it should be apparent that various modifications and changes can be made in the present invention without departing from the spirit and scope of the following claims.

We claim:

1. A personal care absorbent article comprising:

a liquid permeable body side liner, an outer cover and an absorbent core disposed between said body side liner and said outer cover to form said article, said body side liner having an insult time of five seconds or less in accordance with a liquid strike-through test, said article further including a separation layer disposed between said body side liner and said absorbent core, said article having a relative surface moisture value, in accordance with a relative surface moisture test, at approximately one minute after an insult with 80 milliliters of stabilized isotonic 0.9 percent saline solution of 70 percent or greater and a relative surface moisture value, in accordance with the relative surface moisture test, at approximately 10 minutes after said insult of 55 percent or less.

2. The personal care absorbent article of claim 1 wherein said relative surface moisture value at approximately one minute after said insult is 75 percent or greater.

3. The personal care absorbent article of claim 2 wherein said relative surface moisture value at approximately ten minutes after said insult is 50 percent or less.

4. The personal care absorbent article of claim 1 wherein said relative surface moisture value at approximately one minute after said insult is 80 percent or greater.

5. The personal care absorbent article of claim 4 wherein said relative surface moisture value at approximately ten minutes after said insult is 50 percent or less.

6. The personal care absorbent article of claim 4 wherein said relative surface moisture value at approximately ten minutes after said insult is 40 percent or less.

7. The personal care absorbent article of claim 1 wherein said separation layer has a basis weight of about 40 to about 170 grams per square meter, a void volume at 68.9 pascals of about 17 to about 117 cubic centimeters per gram of web, a permeability of about $5.0 \times 10^{-2}$ to about $1.0 \times 10^{-4}$ square centimeters and a surface area per void volume at 68.9 pascals of about 15 to about 90 square centimeters per cubic centimeter.

8. The personal care absorbent article of claim 1 wherein said article is in the form of a training pant.

9. The personal care absorbent article of claim 3 wherein said article is in the form of a training pant.

10. The personal care absorbent article of claim 5 wherein said article is in the form of a training pant.

11. The personal care absorbent article of claim 7 wherein said article is in the form of a training pant.

12. The personal care absorbent article of claim 1 wherein said article is in the form of a diaper.

13. The personal care absorbent article of claim 3 wherein said article is in the form of a diaper.

14. The personal care absorbent article of claim 5 wherein said article is in the form of a diaper.

15. The personal care absorbent article of claim 7 wherein said article is in the form of a diaper.

16. The personal care absorbent article of claim 1 wherein said article is in the form of an incontinence garment.

17. The personal care absorbent article of claim 3 wherein said article is in the form of an incontinence garment.

18. The personal care absorbent article of claim 5 wherein said article is in the form of an incontinence garment.

19. The personal care absorbent article of claim 7 wherein said article is in the form of an incontinence garment.

* * * * *

UNITED STATES PATENT AND TRADEMARK OFFICE
CERTIFICATION OF CORRECTION

PATENT NO. : 5,658,268

DATED : August 19, 1997

INVENTOR(S): Johns et al.

It is certified that errors appear in the above-identified patent and that said Letters Patent is hereby corrected as shown below:

Column 12, line 58, "b 1." should read --1.--;
Column 13, line 5, "3.Starting" should read --3. Starting--;
Column 17, line 67, "92%" should read --82%--;
Column 18, line 9, "outline" should read --outlined--;
Column 20, line 25, "13%" should read --15%--.

Signed and Sealed this

Sixth Day of October, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,658,268
DATED : August 19, 1997
INVENTOR(S) : Johns, et al

It is certified that error appears in the above-identified patent and that said Letters Patent is hereby corrected as shown below:

On the title page, item [73] Assignee, "Irving, Tex." should read -- Neenah, Wis. --

Signed and Sealed this

Thirtieth Day of March, 1999

Attest:

Attesting Officer

Q. TODD DICKINSON

Acting Commissioner of Patents and Trademarks